(12) United States Patent
Tajima et al.

(10) Patent No.: US 10,045,746 B2
(45) Date of Patent: Aug. 14, 2018

(54) RADIATION IMAGE PROCESSING APPARATUS, METHOD, AND MEDIUM

(71) Applicant: FUJIFILM Corporation, Tokyo (JP)

(72) Inventors: Takashi Tajima, Ashigarakami-gun (JP); Jun Enomoto, Ashigarakami-gun (JP); Yasufumi Oda, Ashigarakami-gun (JP); Takeshi Kuwabara, Ashigarakami-gun (JP); Daiki Harada, Ashigarakami-gun (JP); Yuichi Hosoi, Ashigarakami-gun (JP); Noriaki Ida, Ashigarakami-gun (JP); Naoyuki Nishino, Ashigarakami-gun (JP); Haruyasu Nakatsugawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 236 days.

(21) Appl. No.: 14/637,522

(22) Filed: Mar. 4, 2015

(65) Prior Publication Data
US 2015/0251018 A1   Sep. 10, 2015

(30) Foreign Application Priority Data

Mar. 10, 2014 (JP) ................................. 2014-045926
Jul. 31, 2014 (JP) ................................. 2014-156412
Jan. 8, 2015 (JP) ................................. 2015-002058

(51) Int. Cl.
*A61N 5/10* (2006.01)
*A61B 6/00* (2006.01)
*G06T 5/00* (2006.01)

(52) U.S. Cl.
CPC .......... *A61B 6/4233* (2013.01); *A61B 6/5282* (2013.01); *G06T 5/002* (2013.01); *G06T 2207/10116* (2013.01)

(58) Field of Classification Search
CPC ...... A61B 6/4233; A61B 6/5282; G06T 5/002
See application file for complete search history.

(56) References Cited

U.S. PATENT DOCUMENTS

| 5,712,890 A | * | 1/1998 | Spivey | ............. A61B 6/032 378/37 |
| 6,633,626 B2 | * | 10/2003 | Trotter | ............. A61B 6/00 378/37 |

(Continued)

FOREIGN PATENT DOCUMENTS

| JP | 61-133847 A | 6/1986 |
| JP | 02-244811 A | 9/1990 |

(Continued)

OTHER PUBLICATIONS

Christiaan Fivez et al., "Multi-Resolution Contrast Amplification In Digital Radiography With Compensation For Scattered Radiation", IEEE, 1996, pp. 339-342.

(Continued)

*Primary Examiner* — David J Makiya
*Assistant Examiner* — Soorena Kefayati
(74) *Attorney, Agent, or Firm* — Sughrue Mion, PLLC

(57) ABSTRACT

In a radiation image processing apparatus, method, and program, performing image processing based on scattered radiation, such as scattered radiation elimination processing, accurately by taking into account the influence of scattered radiation from an area adjacent to a processing target area. For this purpose, performing image processing on a radiation image captured by applying radiation to a subject based on scattered radiation generated by the subject. In this case, a processing target area which is the processing target in the radiation image is added with another area different from the processing target area in the radiation image. Then, the image processing based on scattered radiation is performed (Continued)

on the processing target area using the another area and the processing target area.

11 Claims, 8 Drawing Sheets

(56) References Cited

U.S. PATENT DOCUMENTS

| | | | | |
|---|---|---|---|---|
| 7,352,887 | B2* | 4/2008 | Besson | G06T 5/008 378/7 |
| 7,396,162 | B1* | 7/2008 | Edic | A61B 6/5282 378/207 |
| 7,760,855 | B2* | 7/2010 | Ruhrnschopf | A61B 6/4035 378/87 |
| 7,889,833 | B2* | 2/2011 | Hagiwara | G06T 11/008 378/4 |
| 7,907,697 | B2* | 3/2011 | Maltz | G06T 11/005 378/7 |
| 7,912,180 | B2* | 3/2011 | Zou | A61B 6/032 378/7 |
| 7,916,829 | B2* | 3/2011 | Harer | A61B 6/032 378/204 |
| 7,945,015 | B2* | 5/2011 | Tsujii | A61B 6/00 378/124 |
| 8,064,676 | B2* | 11/2011 | Li | A61B 6/00 382/132 |
| 8,284,893 | B2* | 10/2012 | Noshi | G06T 11/005 378/7 |
| 8,873,703 | B2* | 10/2014 | Ruimi | A61B 6/032 250/370.09 |
| 8,908,832 | B2* | 12/2014 | Yamashita | A61B 6/06 378/62 |
| 9,084,543 | B2* | 7/2015 | Kobayashi | A61B 6/032 |
| 9,183,621 | B2* | 11/2015 | Takahashi | A61B 6/5258 |
| 9,214,012 | B2* | 12/2015 | Tsuchiya | G06T 5/002 |
| 9,232,925 | B2* | 1/2016 | Hasegawa | G06T 5/002 |
| 9,263,164 | B2* | 2/2016 | Goldammer | A61B 6/4035 |
| 9,427,194 | B2* | 8/2016 | Bouhnik | A61B 6/032 |
| 9,779,520 | B2* | 10/2017 | Suzuki | G06T 11/005 |
| 2002/0109113 | A1* | 8/2002 | Wang | G01T 1/2014 250/584 |
| 2003/0048938 | A1* | 3/2003 | Wang | G01T 1/2014 382/132 |
| 2004/0202360 | A1* | 10/2004 | Besson | G06T 5/008 382/131 |
| 2008/0013673 | A1* | 1/2008 | Ruhmschopf | A61B 6/482 378/7 |
| 2008/0198963 | A1* | 8/2008 | Spahn | A61B 6/4035 378/5 |
| 2009/0202127 | A1* | 8/2009 | Bertram | G06T 11/005 382/131 |
| 2010/0172472 | A1* | 7/2010 | Ermes | A61B 6/4441 378/62 |
| 2010/0239146 | A1* | 9/2010 | Suzuki | G06T 11/005 382/131 |
| 2013/0020476 | A1* | 1/2013 | Mercur'ev | H04N 5/3653 250/252.1 |
| 2013/0259365 | A1* | 10/2013 | Suzuki | G06K 9/4652 382/164 |
| 2013/0315372 | A1* | 11/2013 | Behiels | A61B 6/06 378/62 |
| 2014/0193082 | A1* | 7/2014 | Ohnuki | H04N 1/409 382/205 |
| 2014/0301625 | A1* | 10/2014 | Takahashi | A61B 6/5258 382/132 |
| 2014/0361192 | A1* | 12/2014 | Imai | A61B 6/4291 250/395 |
| 2015/0038834 | A1* | 2/2015 | Gorges | A61B 6/12 600/424 |
| 2015/0063526 | A1* | 3/2015 | Kobayashi | A61B 6/5282 378/4 |
| 2016/0135764 | A1* | 5/2016 | Wojcik | A61B 6/4233 378/62 |

FOREIGN PATENT DOCUMENTS

| | | |
|---|---|---|
| JP | 8-266529 A | 10/1996 |
| JP | 9-022039 A | 1/1997 |
| JP | 2006-068038 A | 3/2006 |

OTHER PUBLICATIONS

John M. Boone et al., "An analytical model of the scattered radiation distribution in diagnostic radiology", Am. Assoc. Phys. Med., Sep./Oct. 1998, pp. 721-725, vol. 15, No. 5.

Communication dated Jan. 31, 2017 from the Japanese Patent Office in counterpart application No. 2015-002058.

* cited by examiner

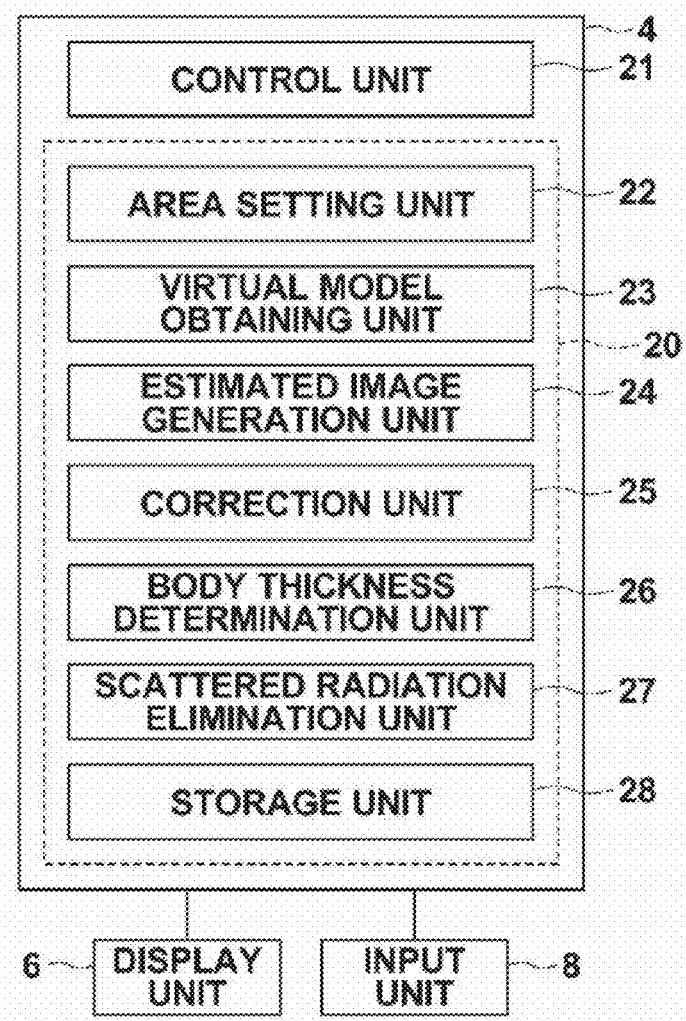
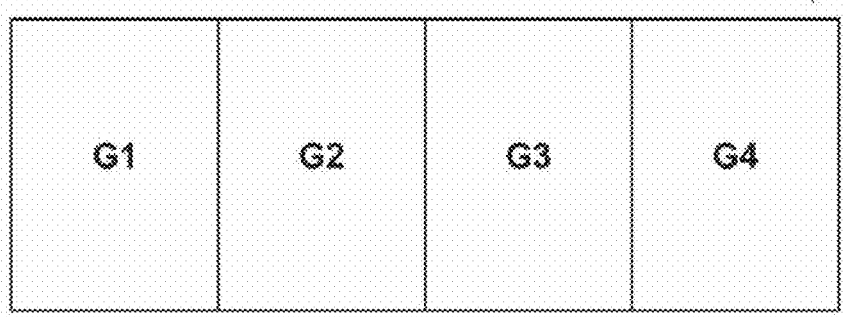

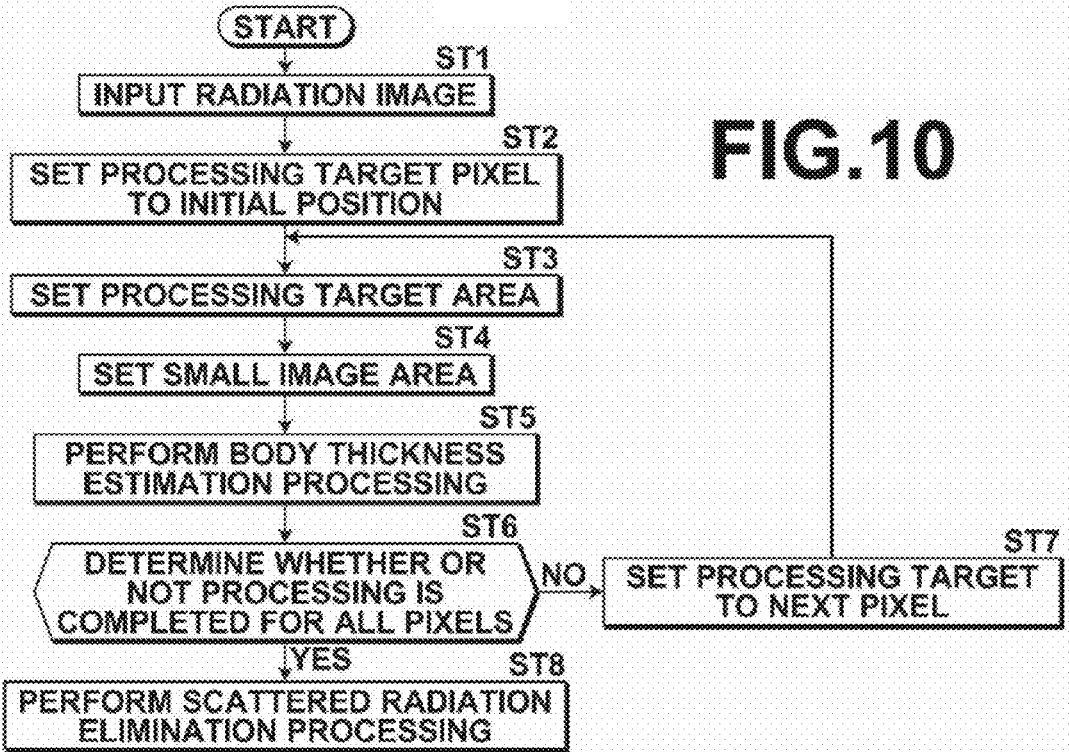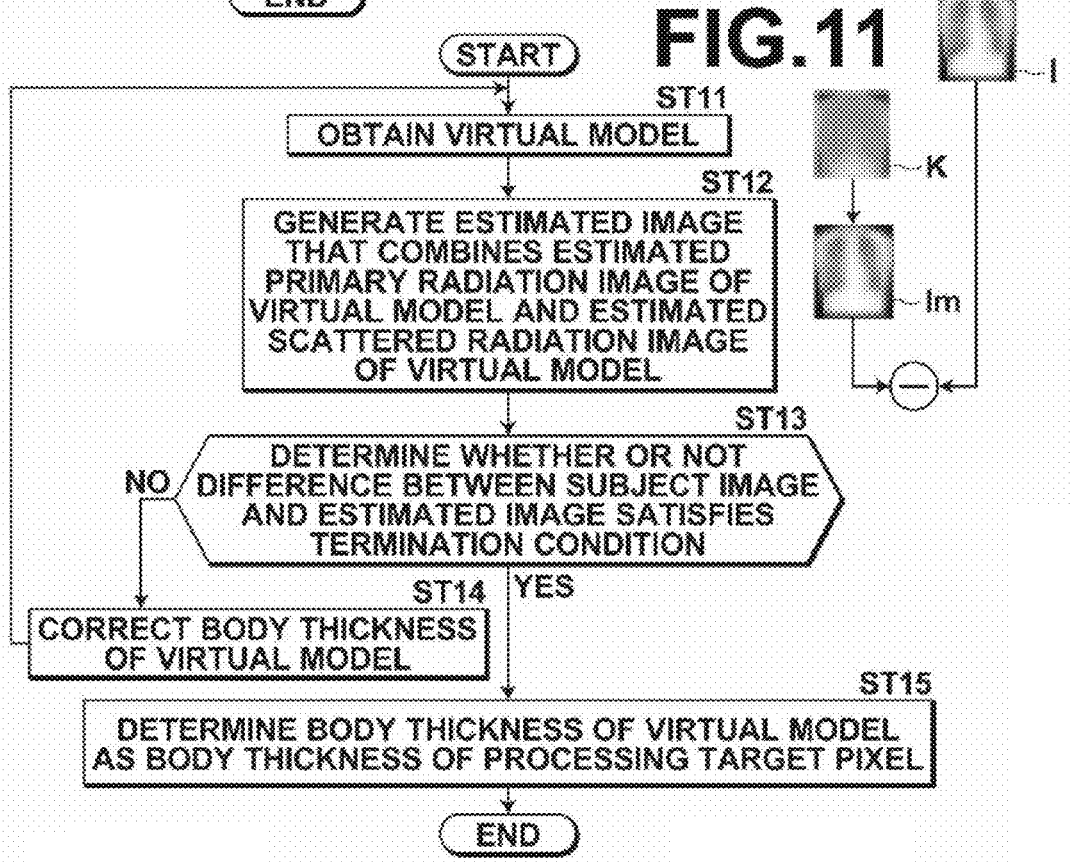

RADIATION IMAGE PROCESSING APPARATUS, METHOD, AND MEDIUM

CROSS-REFERENCE TO RELATED APPLICATIONS

The present application claims priority under 35 U.S.C § 119 to Japanese Patent Application No. 2014-045926 filed on Mar. 10, 2014, Japanese Patent Application No. 2014-156412 filed on Jul. 31, 2014 and Japanese Patent Application No. 2015-002058 filed on Jan. 8, 2015. Each of the above applications is hereby expressly incorporated by reference, in its entirety, into the present application.

BACKGROUND OF THE INVENTION

Field of the Invention

The present invention relates to a radiation image processing apparatus, method, and program for performing image processing based on scattered radiation on a radiation image.

Description of the Related Art

Heretofore, there has been a problem that, in case of capturing a radiation image of a subject by radiation transmitted through the subject, radiation is scattered within the subject, in particular, in case that the subject is thick, whereby scattered radiation is generated and the contrast of the radiation image is reduced by the scattered radiation. Therefore, in order to prevent a radiation detector, which detects radiation and obtains a radiation image, from being exposed to scatted radiation in case of capturing a radiation image, radiography is sometimes performed by disposing an anti-scatter grid (hereinafter, simply "grid") between a subject and the radiation detector. As the radiography with the use of a grid causes the radiation detector less likely to be exposed to radiation scattered from the subject, the contrast of the radiation image may be improved.

The grid is formed by alternately disposing radiopaque lead or the like, and a radiolucent interspace material, such as aluminum, fiber, or the like, with a fine grid density of, for example, about 4.0 lines/mm, so that the grid is weighty. For this reason, in portable radiography performed in a patient room or the like, the grid needs to be disposed between a lying patent and the radiation detector, thereby causing a large burden of deployment work, and heavy strain on the patient at the time of radiography. Further, in the case of a converging grid, density unevenness may possibly occur due to oblique incidence of radiation. Still Further, a fine stripe pattern (moiré) corresponding to the pitch of the grid may sometimes be recorded in a radiation image together with a subject image, thereby making it hard to view the radiation image.

Consequently, it is practiced that a radiation image is captured without using a grid and an image quality improvement effect that can be obtained by removing scattered radiation using a grid is given to the radiation image through image processing, as described, for example, in U.S. Pat. No. 8,064,676 and Non-Patent Literature, C. Fivez et al., "MULTI-RESOLUTION CONTRAST AMPLIFICATION IN DIGITAL RADIOGRAPHY WITH COMPENSATION FOR SCATTERED RADIATION", IEEE, pp. 339-342, 1996. The methods described in U.S. Pat. No. 8,064,676 and Non-Patent Literature, C. Fivez et al., "MULTI-RESOLUTION CONTRAST AMPLIFICATION IN DIGITAL RADIOGRAPHY WITH COMPENSATION FOR SCATTERED RADIATION", IEEE, pp. 339-342, 1996 are a method that frequency-decomposes a radiation image into a plurality of frequency components, then performs scattered radiation elimination processing for eliminating contrast or latitude on a low frequency component which is regarded as a scattered radiation component, and combines the processed frequency components, thereby obtaining a radiation image eliminated of a scattered radiation component. In the method described in U.S. Pat. No. 8,064,676, the scattered radiation elimination processing is performed by multiplying a low frequency component with a gain according to the hierarchy of the low frequency component and the pixel value of the low frequency component. Here, the gain is a value less than 1 and a smaller value is allocated to a lower frequency band or a brighter pixel value. The method described in Non-Patent Literature, C. Fivez et al., "MULTI-RESOLUTION CONTRAST AMPLIFICATION IN DIGITAL RADIOGRAPHY WITH COMPENSATION FOR SCATTERED RADIATION", IEEE, pp. 339-342, 1996 uses a table that converts a low frequency component according to the pixel value thereof and a lower frequency band is more largely suppressed in a geometric progression manner.

According to the methods described in U.S. Pat. No. 8,064,676 and Non-Patent Literature, C. Fivez et al., "MULTI-RESOLUTION CONTRAST AMPLIFICATION IN DIGITAL RADIOGRAPHY WITH COMPENSATION FOR SCATTERED RADIATION", IEEE, pp. 339-342, 1996, strain of a patient may be alleviated at the time of radiography and image quality degradation due to density unevenness and moiré may be prevented, since no grid is required at the time of radiography.

In the meantime, it is known that, in case of capturing a radiation image of a subject by radiation transmitted through the subject, the influence of radiation scattering in the subject, reduced radiation transmission factor, and the like is increased with the increase in the thickness of the subject, and the image quality of the captured radiation image is changed. Consequently, a technology is proposed in which a body thickness which is a thickness of a subject, is roughly estimated by various types of information, such as radiography conditions and signal values of a radiation image, the width of histogram of signal values of the radiation image, or the length of the subject in a predetermined direction in the radiation image, and conditions of image processing, such as scattered radiation elimination processing to be performed on the captured radiation image and the like, or radiography conditions applied to capturing of a radiation image are changed according to the estimated body thickness.

For example, Japanese Unexamined Patent Publication No. 2(1990)-244881 discloses a method in which an association table that associates the relationship between the body thickness and the pixel value is provided by measuring pixel values of an image captured, in advance, by radiography of a simulated subject having a known thickness with known radiography conditions, then the body thickness is roughly estimated according to the pixel values of the radiation image based on the association table, and a scattered component of the radiation image is estimated according to the body thickness of the radiation image, whereby the scattered component is subtracted from the radiation image and a processed image is obtained.

In the meantime, in the radiography performed in the field of medicine, long length radiography with a long length region, such as the entire backbone (entire spine) or the entire leg (entire lower extremity) as the radiography target is sometimes performed. For radiography, various types of radiation detectors (so-called "Flat Panel Detectors") that record a radiation image of a subject by receiving radiation transmitted through the subject have been proposed and put into practical use, but there may be a case in which the radiographable range of the radiation detector is narrower than the target desired to be radiographed. Therefore, in order to perform long length radiography, the radiation detector is moved along a predetermined movement axis so as to partially overlap and radiation transmitted through the same subject is received by the radiation detector each time the position of the detector is changed. Then, a reading operation from the radiation detector is performed with respect to each exposure of radiation (radiation image recording) and a radiation image is captured with respect to each reading operation. Thereafter, the radiation images are combined so as to be joined together, whereby a long radiation image representing a long portion of the subject is obtained.

Note that a radiation detector having a very wide radiographable area (long radiation detector, hereinafter, "long panel") is proposed and the use of such a long panel allows a long radiation image identical to that of the long length radiography to be obtained by one radiography operation. Such long panel appears to be one panel, but a plurality of detectors is disposed inside thereof, joined in series. Then, a radiation image is obtained from each of the plurality of detectors by one exposure of radiation, and the plurality of radiation images obtained is combined with the use of software or the like, whereby a radiation image having a size larger than that of the individual radiation detectors may be obtained.

In the meantime, there may be a case in which a portion of a radiation image which is an observation target is trimmed and displayed. In such a case, image processing is performed on the trimmed area to improve the image quality of the area. For example, Japanese Unexamined Patent Publication No. 2006-068038 proposes a method in which an image processing parameter for an area to be extracted is obtained and image processing is performed on the trimmed area using the image processing parameter.

SUMMARY OF THE INVENTION

In the meantime, it is possible to perform image processing based on scattered radiation, such as body thickness estimation processing, scattered radiation elimination processing, or the like on the long radiation image described above. In this case, it is conceivable that the image processing based on scattered radiation is performed on each radiation image having a small size corresponding to each detector (hereinafter, "small radiation image") in the long radiation image. It is difficult to accurately eliminate a scattered radiation component at a boundary portion of a small radiation image using only the small radiation image, since the scattered radiation component is influenced by a scattered radiation component included in an adjacent small radiation image. This is a problem that also occurs in a long radiation image or in case that a radiation image obtained by one radiation detector is trimmed and scattered radiation elimination processing is performed on the trimmed image.

In this case, it is conceivable that the image processing based on scattered radiation is performed after combining the small radiation images so as to be joined together. But the combined radiation image has a very large size, resulting in an extremely large amount of computation and a prolonged time for the processing.

The present invention has been developed in view of the circumstances described above, and it is an object of the present invention to accurately perform image processing based on scattered radiation in a radiation image processing apparatus, method, and program, by taking into account the influence of scattered radiation from an area adjacent to a processing target area.

It is a further object of the present invention to perform image processing based on scattered radiation by reducing the amount of computations.

A radiation image processing apparatus according to the present invention is an apparatus that performs image processing on a radiation image captured by applying radiation to a subject based on scattered radiation generated by the subject, the apparatus including:

an area setting means that, in performing the image processing on a processing target area of the image processing in the radiation image, adds another area different from the processing target area in the radiation image to the processing target area; and an image processing means that performs the image processing on the processing target area using the another area and the processing target area.

The "image processing based on scattered radiation" refers to any processing as long as it uses scattered radiation component information included in a radiation image, and the image processing based on scatted radiation may include, for example, body thickness estimation processing that estimates a body thickness of a subject using scattered radiation component information, scattered radiation elimination processing that eliminates scattered radiation from the processing target area using the estimated body thickness, and the like. Further, the processing that enhances the contrast of a radiation image using scattered radiation component information may also be the image processing based on scattered radiation.

The "another area" refers to any area as long as it is different from a processing target area in a radiation image and, for example, in case that one radiation image is formed of a plurality of radiation images, as in a radiation image obtained by a long panel and a radiation image obtained by long length radiography, and each radiation image is set as the processing target area, at least one radiation image different from each radiation image set as the processing target area may be the another area. In case that a partial area of a radiation image is set as the processing target area, an area other than the processing target area may be the another area. Here, the radiation image may be a radiation image formed of a plurality of radiation images, as in a radiation image obtained by a long panel and a radiation image obtained by long length radiography, or a radiation image obtained using one radiation detector.

In the radiation image processing apparatus according to the present invention, in case that the radiation image is formed of a plurality of small radiation images smaller in area than the radiation image and one of the small radiation images is set as the processing target image, the area setting means may be a means that adds at least one another small radiation image different from the small radiation image set as the processing target image to the processing target area as the another area.

The "radiation image is formed of a plurality of small radiation images" refers to that one radiation image may be formed of a plurality of small radiation images combined with each other or one radiation image may be formed of a plurality of small radiation images spaced apart from each other. Further, in case that a plurality of small radiation images is combined, one radiation image may be formed by partially overlapping the plurality of small radiation images or one radiation image may be formed by arranging the plurality of small radiation images without any gap.

Further, in the radiation image processing apparatus according to the present invention, the at least one another small radiation image may be a small radiation image adjacent to the small radiation image set as the processing target image.

The "adjacent to" refers to a small radiation image of a plurality of small radiation images constituting a radiation image located at a position closest to the small radiation image set as the processing target.

Still further, in the radiation image processing apparatus according to the present invention, the image processing means may be a means that performs the image processing in priority order from a small radiation image corresponding to a thick body portion of the subject.

Further, in the radiation image processing apparatus according to the present invention, a radiation image may be formed of a plurality of small radiation images combined together.

Still further, in the radiation image processing apparatus according to the present invention, in case that the radiation image is formed of the small radiation images combined so as to partially overlap with each other and an abnormality occurs in a result of the image processing in an area where the small radiation images are overlapped, the image processing means may be a means that performs the image processing using an adjacent area adjacent to the area where the small radiation images are overlapped.

Further, in the radiation image processing apparatus according to the present invention, the area setting means may be a means that, in performing the image processing on the processing target area, further sets a small image area smaller than the processing target area for a processing target pixel in the processing target area, and the image processing means may be a means that performs the image processing based on information of the small image area.

Still further, in the radiation image processing apparatus according to the present invention, the area setting means may be a means that sets the small image area according to the position of the processing target pixel.

Further, in the radiation image processing apparatus according to the present invention, the area setting means may be a means that sets the small image area having a size according to a body thickness or a radiography region of a subject in the processing target area.

Still further, in the radiation image processing apparatus according to the present invention, the image processing means may be a means that performs the image processing on another image area using a parameter of the image processing performed on one small image area.

A radiation image processing method according to the present invention is a method that performs image processing on a radiation image captured by applying radiation to a subject based on scattered radiation generated by the subject, the method including the steps of:

in performing the image processing on a processing target area of the image processing in the radiation image, adding another area different from the processing target area in the radiation image to the processing target area; and performing the image processing on the processing target area using the another area and the processing target area.

Note that the radiation image processing method according to the present invention may be provided as a program to be executed by a computer.

In performing image processing on a radiation image based on scattered radiation, as the processing target area of the image processing is influenced by a scattered radiation component included in an area surrounding the processing target area, the performance of the image processing based on scattered radiation using only the processing target area results in that the image processing cannot be performed accurately. According to the present invention, in performing image processing on a processing target area based on scattered radiation, another area different from the processing target area in the radiation image is added to the processing target area, and the image processing based on scattered radiation is performed on the processing target area using the another area and the processing target area. This allows the image processing based on scattered radiation to be performed on the processing target area by taking into account the influence of a scattered radiation component included in the another area, whereby the image processing based on scattered radiation may be performed accurately on the processing target area.

BRIEF DESCRIPTION OF THE DRAWINGS

FIG. 3 is a schematic block diagram of a computer in control system, illustrating a configuration thereof.

FIG. 4 illustrates setting of a processing target area.

FIG. 10 is a flowchart illustrating processing steps performed in the first embodiment.

FIG. 11 is a flowchart illustrating body thickness estimation processing steps.

DETAILED DESCRIPTION OF THE PREFERRED EMBODIMENTS

Figure 1:
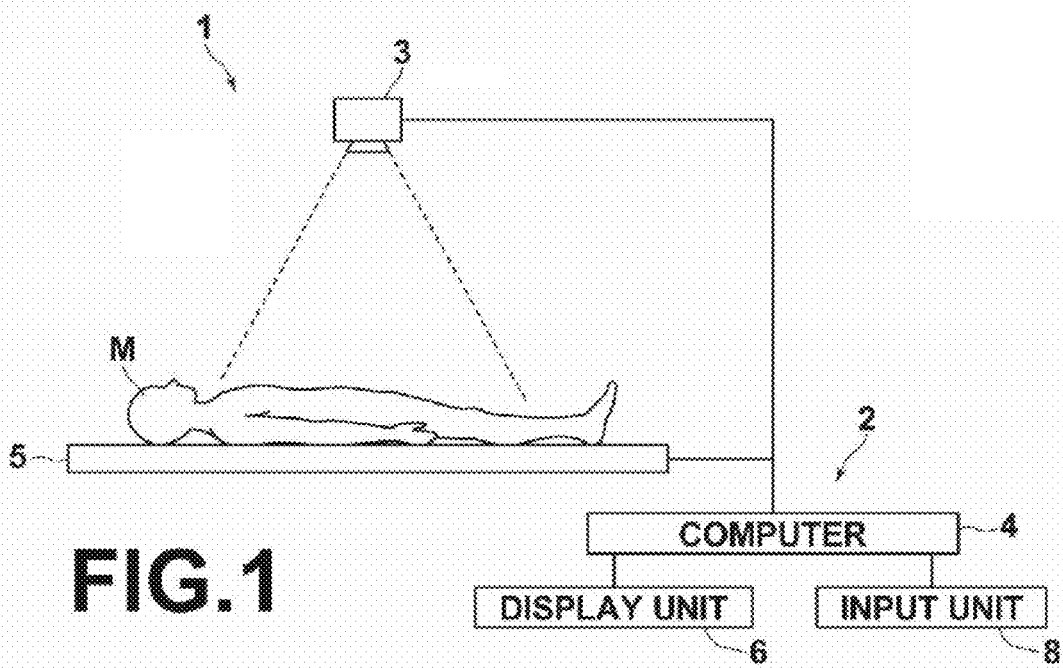
FIG. 1 is a schematic block diagram of a radiation image capturing system to which a radiation image processing apparatus according to a first embodiment of the present invention is applied, illustrating a configuration thereof.

Hereinafter, embodiments of the present invention will be described with reference to the accompanying drawings. FIG. 1 is a schematic block diagram of a radiation image capturing system to which a radiation image processing apparatus according to a first embodiment of the present invention is applied, illustrating a configuration thereof. As illustrated in FIG. 1, the radiation image capturing system according to the first embodiment is a system for performing image processing based on scattered radiation on a radiation image of a subject, more specifically, the system performs subject body thickness estimation processing and scattered radiation elimination processing to eliminate scattered radiation from the radiation image and improving the contrast. As illustrate in FIG. 1, the radiation image capturing system includes a radiography system 1 and a control system 2 that includes a radiation image processing apparatus according to the present embodiment.

The radiography system 1 includes an X-ray source 3 that applies X-rays to a subject M and a radiation detector 5 that detects X-rays transmitted through the subject M and obtains a radiation image of the subject M.

The radiation detector 5 can be used repeatedly for recording and reading of a radiation image, and a so-called direct type radiation detector that generates a charge by directly receiving radiation may be used or a so-called indirect type radiation detector that tentatively converts the radiation to visible light and converts the visible light to a charge signal may be used. As for the readout method of the radiation image signal, a so-called TFT (thin film transistor) readout method in which radiation image signals are read out by ON/OFF switching TFT switches or a so-called optical readout method in which radiation image signals are read out by applying reading light is preferably used, but not limited to this and the other method may be used. Further, a CMOS (Complementary Metal Oxide Semiconductor) image sensor may also be used.

Figure 2:
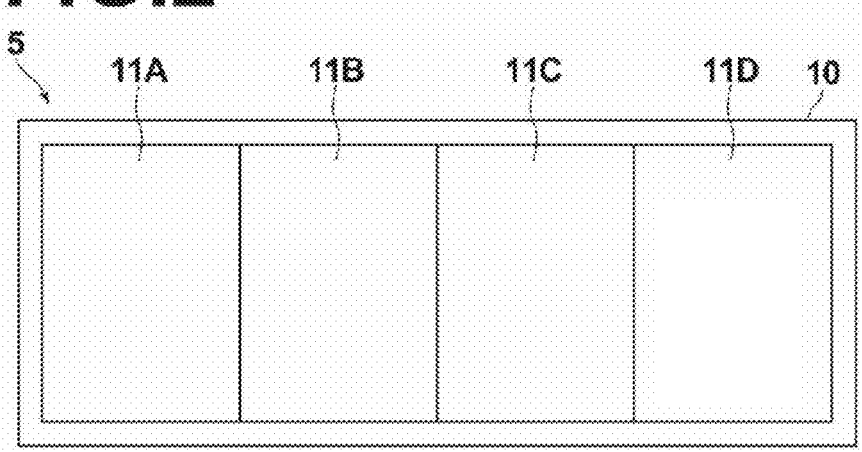
FIG. 2 illustrates a configuration of the radiation detector used in the present embodiment.

The radiation detector used in the present embodiment is a long radiation detector capable of obtaining a radiation image of the entire backbone (entire spine), the entire leg (entire lower extremity) of a human body, or the like by one radiography operation. FIG. 2 illustrates a configuration of the radiation detector 5 used in the present embodiment. As illustrated in FIG. 2, the radiation detector 5 used in the present embodiment is formed of a plurality of (four in the present embodiment) detectors 11A to 11D disposed in series in a long panel 10. The detectors 11A to 11D are preferably disposed such that portions thereof between adjacent detectors overlap with each other in order to prevent a radiation image from being discontinued.

The radiation detector 5 is connected to the control system 2 via a cable or the like, or by way of radio. The radiation image reading operation from the radiation detector 5 is performed on a detector by detector basis, but the radiation images are processed as one radiation image in the control system 2, as will be described later.

The control system 2 includes a computer 4, and a display unit 6 and an input unit 8 connected to the computer 4.

The computer 4 includes a CPU (Central Processing Unit), a semiconductor memory, a communication interface, a storage device, such as a hard disk, a SSD (Solid State Drive), or the like, and these pieces of hardware forms a control unit 21, area setting unit 22, a virtual model obtaining unit 23, an estimated image generation unit 24, a correction unit 25, a body thickness determination unit 26, a scattered radiation elimination unit 27, and a storage unit 28, as shown in FIG. 3. Note that the area setting unit 22, virtual model obtaining unit 23, estimated image generation unit 24, correction unit 25, body thickness determination unit 26, scattered radiation elimination unit 27, and storage unit 28 constitute a radiation image processing apparatus 20 of the present invention.

The control unit 21 controls the X-ray source 3 and the radiation detector 5 for performing radiography, reads out radiation images from the radiation detector 5, and controls the entire processing performed in the computer 4.

Figure 5:
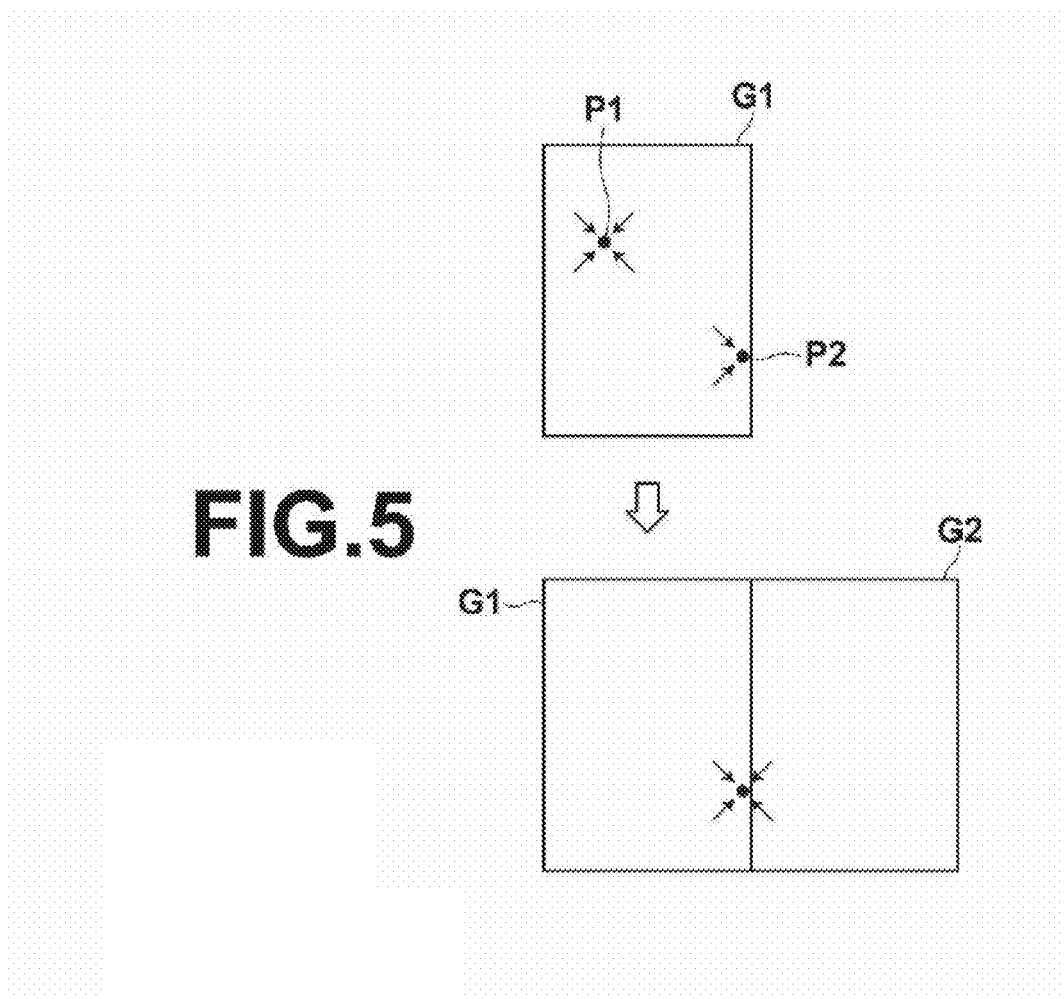
FIG. 5 illustrates setting of a processing target area.

The area setting unit 22 sets a processing target area for performing image processing based on scattered radiation, to be described later, in a radiation image obtained by the radiation detector 5. Further, with respect to a processing target pixel in the processing target area, the unit 22 sets a small image area which is smaller than the processing target area. Hereinafter, setting of the processing target area and the small image area will be described. FIGS. 4 and 5 illustrate setting of a processing target area. In the present embodiment, the radiation detector 5 is a long radiation detector formed of four detectors 11A to 11D disposed inside thereof. Therefore, as shown in FIG. 4, the radiation image G0 is generated in effect by combining small sized four small radiation images G1 to G4.

Here, a scattered radiation component at a certain pixel position in a radiation image is influenced by scattered radiation components included in images of areas surrounding the pixel position. For example, the scattered radiation component at the pixel P1 in the radiation image G1 shown in FIG. 5 is influenced by scattered radiation components included in images of surrounding areas, as illustrated by the arrows around the pixel P1. As the pixel P1 is located at a position away from an end of the radiation image G1, the use of only the information of the radiation image G1 in performing image processing based on scattered radiation component allows the scattered radiation to be eliminated accurately. In the meantime, as the pixel P2 in the radiation image G1 is located at a position close to an end of the radiation image G1, the use of only the information of the radiation image G1 does not allow the scattered radiation to be eliminated accurately, since all of the scattered radiation components that influence the pixel P2 cannot be taken into account. For this reason, in the present embodiment, in eliminating scattered radiation for a pixel in the radiation image G1, the area setting unit 22 sets the processing target area by adding the radiation image G2 to the processing target area. This results in that image processing based on scattered radiation is performed on the pixel P2 using information of the radiation image G2 adjacent the radiation image G1, in addition to the radiation image G1, that is, using the information of the radiation image G1 and the radiation image G2, as illustrated in FIG. 5.

Note that, in performing image processing based on scattered radiation on a pixel in the radiation image G1, the radiation images G2 and G3, as well as the radiation image G1, may be added to the processing target area, or all of the radiation images G2 to G4 may be added to the processing target area. Further, in performing image processing based on scattered radiation on a pixel in the radiation image G2, only the radiation image G1 may be added to the processing target area, only the radiation image G3 may be added to the processing target area, radiation images G1 and G3 may be added to the processing target area, or radiation images G1, G3, and G4 may be added to the processing target area. Still further, in performing image processing based on scattered radiation on a pixel in the radiation image G3, only the radiation image G2 may be added to the processing target area, only the radiation image G4 may be added to the processing target area, radiation images G2 and G4 may be added to the processing target area, or radiation images G1, G2, and G4 may be added to the processing target area. Further, in performing image processing based on scattered radiation on a pixel in the radiation image G4, only the radiation image G3 may be added to the processing target area, radiation images G2 and G3 may be added to the processing target area, or radiation images G1 to G3 may be added to the processing target area.

In performing image processing based on scattered radiation on the radiation image G2 or G3, a radiation image to be added to the processing target area may be set according to the position of the processing target pixel. For example, in performing image processing based on scattered radiation on the radiation image G2, in case that the processing target pixel is located at a position close to the radiation image G1, only the radiation image G1 may be added to the processing target area, and in case that the processing target pixel is located at a position close to the radiation image G3, only the radiation image G3 may be added to the processing target area.

Figure 6:
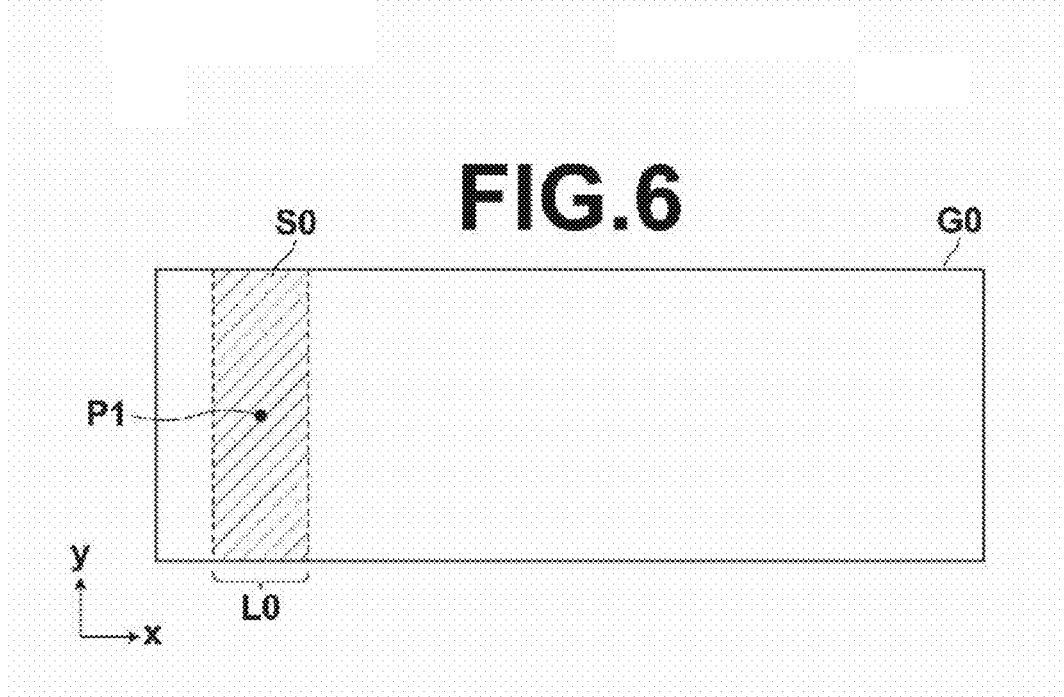
FIG. 6 illustrates setting of a small image area.

With respect to a processing target area, the area setting unit 22 further sets a small image area smaller than the processing target area. FIG. 6 illustrates setting of a small image area. As illustrated in FIG. 6, in case that the lateral direction of the radiation image G0 is taken as y-direction and a direction orthogonal to the lateral direction is taken as x-direction, the area setting unit 22 sets a small image area S0 having a width L0 (e.g., width of 100 pixels) corresponding to the component in the x-direction with the processing target pixel P1 as the center. In FIG. 6, the width L0 is depicted wider than the actual width for the purpose of explanation. The height corresponding to the component of the S0 in the y-direction is the same as the height corresponding to the component of the radiation image G0 in the y-direction. By setting the small image area S0 in this way, the image processing for a processing target pixel is performed using a radiation image in the small image area S0 set for the pixel. Further, near a boundary of small radiation images G1 to G4, two small radiation images extending across the boundary are included in the small image area S0, so that scattered radiation may be eliminated accurately by the use of information of the small image area S0.

Figure 7:
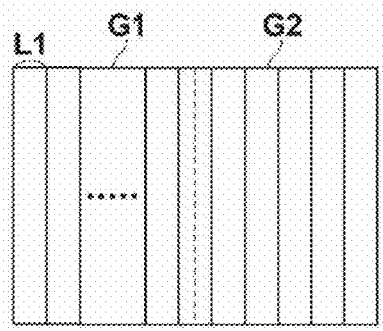
FIG. 7 illustrates setting of a small image area.

The small image area S0 may be set each time the position of a pixel to be a processing target (processing target pixel) is changed. Further, as illustrated in FIG. 7, in case that the processing target area is set to the radiation images G1 and G2, small image areas S0 may be set by equally dividing the processing target area into predetermined widths L1 such that the boundary of the radiation images G1 and G2 is included in a small image area. In this case, the image processing for a pixel of the processing target is performed using the information of the small image area S0 in which the pixel is included.

Figure 8:
FIG. 8 illustrates setting of a small image area.

The height of the small image area S0 may not be the same as that of the radiation image G0. For example, as illustrated in FIG. 8, a rectangular area having a predetermined size (L2×L2, L2 corresponds to e.g., 10 pixels) centering on the processing target pixel P1 may be set as a small image area S0.

Figure 9:
FIG. 9 illustrates setting of a small image area.

The size of the small image area S0 may be set according to the body thickness or the radiography region of the subject M. For example, in case that the subject M includes, in large part, abdominal and chest regions of a human body having a large body thickness, scattered radiation increases and spreads out extensively. Therefore, a small image area S0 having a larger size, as illustrated in FIG. 9, may eliminate the scattered radiation more efficiently. On the other hand, in case that the subject M is thin, like an extremity having a thin body, scattered radiation decreases and the scattered radiation may be eliminated even with a small image area S0 having a small size.

The body size of the subject M may be inputted by the operator from the input unit 8. Otherwise, an arrangement may be adopted in which a body thickness measuring device, such as an optical sensor or the like, is provided in the radiography system 1, then a measured value of the device is inputted to the computer 4, and the size of the small image area S0 is set by the area setting unit 22 based on the measured value.

The virtual model obtaining unit 23 obtains a virtual model K of the subject M having an initial body thickness T0 (given body thickness) distribution in performing body thickness estimation processing.

Based on the virtual model K, the estimated image generation unit 24 generates an image that combines an estimated primary radiation image Ip estimating a primary radiation image that can be obtained by radiography of the virtual model and an estimated scattered radiation image Is estimating a scattered radiation image that can be obtained by radiography of the virtual model, as an estimated image Im estimating a radiation image that can be obtained by radiography of the subject M.

Based on the estimated image Im and the radiation image G0, the correction unit 25 corrects the initial body thickness T0 of the virtual model K such that the difference between the estimated image Im and the radiation image G0 is reduced.

The body thickness determination unit 26 determines a corrected body thickness Tn−1 (n is natural number) as a body thickness Tk of the subject included in the radiation image.

The scattered radiation elimination unit 27 performs scattered radiation elimination processing using the determined body thickness Tk and eliminates scattered radiation from the radiation image G0.

In the present embodiment, the virtual model K of the subject M having the initial body thickness T0 (x,y) distribution is stored in the storage unit 28. The "body thickness" refers to a total subject area thickness other than an air area in the path of applied radiation.

Next, processing performed in the first embodiment will be described. FIG. 10 is a flowchart illustrating the steps of processing performed in the first embodiment. When radiography of the subject M is performed and a radiation image is inputted to the computer 4 (step ST1), the control unit 21 sets a processing target pixel (x,y) to an initial position (step ST2). Then, the area setting unit 22 sets a processing target area for the determined processing target pixel (step ST3), and further sets a small image area S0 for the processing target pixel (step ST4). Then, the radiation image processing apparatus 20 performs body thickness estimation processing based on a radiation image in the small image area S0 (step ST5).

FIG. 11 is a flowchart illustrating the steps of the body thickness estimation processing. The virtual model obtaining unit 23 of the radiation image processing apparatus 20 obtains a virtual model K of the subject M having an initial body thickness T0 (x,y) corresponding to the processing target pixel in the small image area S0 from the storage unit 28 (step ST11). The virtual model K may be obtained by relating a body thickness according to the initial body thickness T0 (x,y) to each position in an x-y plane, and represents data that virtually indicate a body thickness of the subject M. Note that the structures (anatomical structures, such as lung field, bone, organ, and the like) included in the virtual model K, the dispositions of the structures, and the characteristic information representing characteristics of the structures with respect to radiation have been set based the dispositions and compositions of anatomical structures, such as the lung field, bone, and the like of the thoracoabdominal region of a comparative subject.

The initial body thickness T0 (x,y) of the virtual model K may be any arbitrary value and the initial body thickness T0 is generated and obtained by the virtual model obtaining unit 23 in the present embodiment. The virtual model obtaining unit 23 obtains radiography conditions, such as radiography dose of the subject M, tube voltage, SID (Source Image receptor Distance), and the like, and obtains a table that associate the pixel value according to the radiography conditions of the subject M with the body thickness from the storage unit 28. Then, the virtual model obtaining unit 23 obtains the body thickness of the processing target pixel of the subject M based on the obtained table. Then, the virtual model obtaining unit 23 obtains the body thickness of the processing target pixel as the initial body thickness T0 of the virtual mode K. Note that the initial body thickness T0 may be generated in the virtual model K obtaining processing, as in the present embodiment, or may be generated before the virtual model K obtaining processing. The foregoing processing can be represented by a formula (1) given below. Here, I (x,y) represents the pixel value of the processing target pixel in the small image area S0 of the radiation image, and T0 (x,y) represents the initial body thickness at the processing target pixel position.

$$T_0(x,y) = \text{LUT}(I(x,y)) \quad (1)$$

Figure 12:
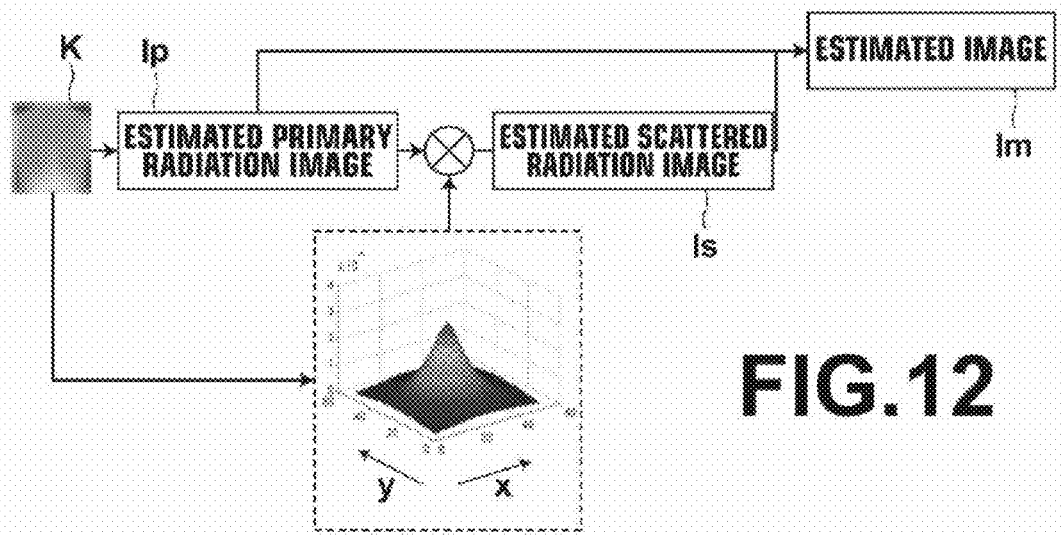
FIG. 12 illustrates an example of estimated image generation method.
Figure 13:
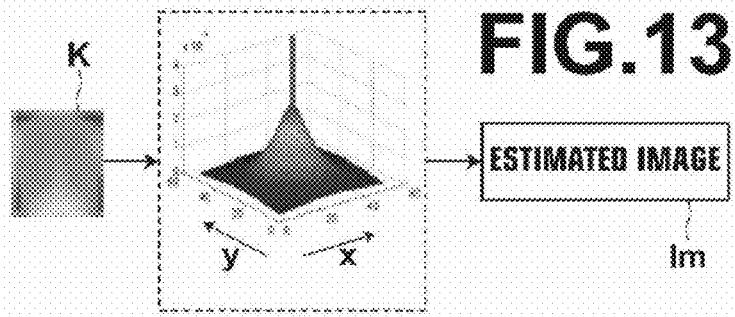
FIG. 13 illustrates another example of estimated image generation method.

Next, the estimated image generation unit 24 generates an estimated image Im that combines an estimated primary radiation image Ip that can be obtained by radiography of the virtual model K with radiography conditions equivalent to those of the radiation image and an estimated scattered radiation image Is that can be obtained by radiography of the virtual model K with radiography conditions equivalent to those of the radiation image (step ST12). Note that, in the following description, the pixel value of the processing target pixel will sometimes be referred to also as the "image". FIGS. 12 and 13 illustrate estimated image Im generation methods.

As illustrated in FIG. 12, the estimated image generation unit 24 generates an estimated primary radiation image Ip with respect to the processing target pixel in the small image area S0 that can be obtained by radiography of the virtual model K with radiography conditions equivalent to those of the radiation image according to a formula (2) given below, and generates an estimated scattered radiation image Is according to a formula (3) given below using the generated estimated primary radiation image Ip. Then, the estimated image generation unit 24 generates an estimated image Im with respect to the processing target pixel by combining the estimated primary radiation image Ip and the estimated scattered radiation image Is, as shown in a formula (4). Note that in the case in which an estimated primary radiation image Ip and an estimated scattered radiation image Is are generated for the first time, the initial body thickness T0 (x,y) is used in the estimation formulae (2) and (3) (n=1 in formulae (2) and (3)).

$$I_p(x, y) = I_o(x, y) \times \exp(-T_{n-1}(x, y) \times \mu) \quad (2)$$

$$I_s(x, y) = \sum_{x',y'} I_p(x', y') K_s(x, y, T_{n-1}(x', y'), \theta_{x',y'}) \quad (3)$$

$$I_m(x, y) = I_p(x, y) + I_s(x, y) \quad (4)$$

Where: (x,y) is the coordinate of the processing target pixel; Ip (x,y) is the estimated primary radiation image at the processing target pixel (x,y); Is (x,y) is the estimated scattered radiation image at the processing target pixel (x,y); Io (x,y) is the dose at the processing target pixel (x,y); Im (x,y) is the estimated image at the processing target pixel (x,y); μ is the linear attenuation coefficient of the subject; and Ks (x, y, Tn (x', y'), θx', y') is the convolution kernel representing the point spread function according to the subject thickness at the processing target pixel (x,y). Here, the convolution is performed using pixel values of pixels in the small image area S0. The dose Io (x,y) is the dose of radiation at the processing target pixel detected by the radiation detector 5 on the assumption that no subject is present, and varies with the distance between the X-ray source 3 and the detection surface of the radiation detector 5 (SID), tube voltage, and mAs value. The θx',y' represents a parameter that can be identified by the radiography conditions, such as the tube voltage and the like, and the characteristic information of the virtual model K.

Note that the estimated image Im may be any image that can be estimated as being obtained in case that the virtual mode K is radiographed and can be deemed substantially as an image that combines an estimated primary radiation image Ip and an estimated scattered radiation image Is. For example, the estimated image Im may be generated by performing convolution integral of the kernel combining the primary radiation component and the scattered radiation component, as illustrated in FIG. 13, using a formula (5) given below, instead of the formulae (2) to (4). Where, $K_p+s(x, y, T_{n-1}(x', y), \theta x; y')$ is the kernel representing the point spread function that combines the primary radiation component and the scattered radiation component. Further, any model function may be used as long as it allows an estimated image that combines an estimated primary radiation image and an estimated scattered radiation image to be obtained from an image obtained by radiography.

Ks(x, y, Tn (x',y'), θx', y') and $K_{p+s}$(x, y, Tn−1 (x', y'), θx', y') can be experimentally obtained according to the radiography conditions and the like.

Kernels Ks(x, y, Tn (x', y'), θx', y') and Kp+s(x, y, Tn−1 (x', y'), θx', y') may be calculated based on radiography conditions at the time of radiography, but in the present embodiment, a table associating various radiography conditions with kernels Ks (x, y, Tn (x', y'), θx', y') and Kp+s(x, y, Tn−1 (x', y'), θx', y') is stored in the storage unit 28, and kernels Ks(x, y, Tn (x', y'), θx', y') and Kp+s(x, y, Tn−1 (x',y'), θx', y') are obtained with reference to the table based on the radiation field at the time of radiography, subject information, and radiography conditions.

$$I_m(x, y) = \sum_{x',y'} K_{p+s}(x, y, T_{n-1}(x', y'), \theta_{x',y'}) \quad (5)$$

The subsequent processing steps will be described according to the flowchart of FIG. 11. Subsequently, the body thickness determination unit 26 determines whether or not the difference between the radiation image and the estimated image Im at the processing target pixel satisfies a termination condition (step ST13). Here, as illustrated in formulae (6) and (7), an error value Verror representing a difference between the radiation image and the estimated image Im described below is defined and a determination is made, as the termination condition, as to whether or not the error value Verror is less than or equal to a threshold value. Further, as shown in the formula (7), a square sum of each pixel value of a differential image Id obtained by subtracting the estimated image Im from the radiation image is defined as an error function ferror. Note that any determination method may be used as long as it is capable of determining, as the termination condition, that the difference between the radiation image and the estimated image Im is sufficiently small.

$$V_{error} = f_{error}(I_m(x, y), I(x, y)) \qquad (6)$$

$$f_{error}(I_m(x, y), I(x, y)) = \sum_{x,y}(I_m(x, y) - I(x, y))^2 \qquad (7)$$

Further, the error function using a steepest descent method e defined, not limited to the foregoing example, by any method that represents a difference between the radiation image and the estimated image Im. For example, as shown in a formula (8) given below, a sum of absolute value of each pixel value of the differential image Id obtained by subtracting the estimated image Im from the radiation image may be defined as an error function ferror.

$$f_{error}(I_m(x, y), I(x, y)) = \sum_{x,y}|I_m(x, y) - I(x, y)| \qquad (8)$$

In case that the error value Verror does not satisfy the termination condition (step ST13: No), the body thickness determination unit 26 performs correction processing to correct the body thickness distribution Tn−1 (in case of n=1, initial body thickness T0) (step ST14).

In order to perform correction of the body thickness Tn−1, any method may be applied as long as it is capable of obtaining a correction value of the body thickness Tn−1 that reduces the difference between the radiation image and the estimated image Im. In the present embodiment, body thickness calculation for partial areas is performed to reduce the difference between the estimated image Im and the radiation image by changing the body thickness Tn−1 of the virtual model K with respect to each small image area. Then, the body thickness distribution of the virtual model is corrected by the calculated body thickness of each partial area.

More specifically, in the present embodiment, a correction value of the body thickness Tn−1 is obtained using the steepest descent method. The output value of the error function ferror may be minimized by calculating dTn−1 by changing the body thickness of only one specific coordinate, in the Tn−1 (x,y), of the pixels of the virtual model K using formulae (9) and (10) and repeating based on the first derivative (slope) of the error function ferror. Then, the body thickness of the processing target pixel when the output value of the error function ferror is minimized is determined as a correction value of the body thickness.

$$T_n(x, y) = T_{n-1}(x, y) - \alpha dT_{n-1}(x, y) \qquad (9)$$
$$= T_{n-1}(x, y) - \alpha \frac{d}{dT_{n-1}(x, y)} f_{error}$$

$$\frac{d}{dT_{n-1}(x, y)} f_{error} = \qquad (10)$$
$$\sum_{x',y'}(I_m(x', y') - I(x', y'))\frac{d}{dT_{n-1}(x, y)}K_{p+s}(x', y', T_{n-1}(x, y), \theta_{x,y})$$

$$\frac{d}{dT_{n-1}(x, y)}K_{p+s}(x', y', T_{n-1}(x, y), \theta_{x,y}) = \qquad (11)$$
$$K_{p+s}(x', y', T_{n-1}(x, y) + dt, \theta_{x,y}) - K_{p+s}(x', y', T_{n-1}(x, y), \theta_{x,y})$$

In the formula (9), α is an update coefficient, which is a parameter representing an update rate of the body thickness. As an example of the calculation method of the derivative value portion of Kp+s shown in the formula (10), for example, a value change when a very small value dt is added to the Tn−1 (x,y) may be calculated by the formula (11) and used as the value of the Kp+s of the formula (10). Note that in the formulae (1) to (11), identical elements are given the same symbols and the explanations are omitted. Any optimization method for minimizing the error value Verror representing the difference between the radiation image and the estimated image Im may be applied, and, for example, simplex method, steepest descent method, or conjugate gradient method may be used.

When the corrected body thickness distribution Tn is obtained, the body thickness determination unit 26 updates the value of n by incrementing by one (n=n+1), and the virtual model obtaining unit 23 obtains the corrected body thickness Tn (step ST11). Then, with respect to the obtained body thickness Tn, the estimated image generation unit 24 and the body thickness determination unit 26 perform the processing of the step ST11 to step ST13 in the same manner as described above. Then, the body thickness Tn correction processing (step ST14), the virtual model having the corrected body thickness Tn obtaining processing (step ST11), the new estimated image Im generation processing using the body thickness Tn (step ST12), and the determination processing as to whether or not the difference between the newly generated estimated image Im and the radiation image satisfies the termination condition (step ST13) are repeated in the same manner as described above until the error value Verror representing the difference between the radiation image and the estimated image Im satisfies the termination condition.

In the meantime, in case that a determination is made that the error value Verror satisfies the termination condition (step ST13: Yes), the body thickness determination unit 26 determines the body thickness Tn used for the error value Verror when the termination condition is satisfied as the body thickness Tk of the processing target pixel, and terminates the body thickness estimation processing for the processing target pixel (step ST15).

Returning to FIG. 10, following the body thickness estimation processing for the processing target pixel, the control unit 21 determines whether or not the processing is completed for all pixels (step ST6). In case that the step ST6 is negative, the control unit 21 sets the processing target to the next pixel (step ST7), and the processing of the step ST3 to the step ST6 is repeated. As the processing target pixel is often adjacent to the processing target pixel of the preceding processing, the body thickness estimation processing may be performed using the parameters (e.g., values of initial body thickness, convolution kernel, and the like) used for the body thickness estimation in the preceding processing. For example, the body thickness Tn estimated in the preceding processing may be used as the initial body thickness T0 (x,y) and the kernel Ks (x, y, Tn (x', y'), θx', y') used in the preceding processing may be used.

In case that step ST6 is positive, scattered radiation elimination processing is performed using the estimated body thickness (step ST8). Hereinafter, the scattered radiation elimination processing will be described. In the scattered radiation elimination processing, a small image area S0 is set for the processing target pixel, as in the body thickness estimation processing. The scattered radiation elimination unit 27 calculates a primary radiation image and a scattered radiation image from the body thickness T (x,y) at the processing target pixel in the radiation image G0 according to formulae (12) and (13) given below, and calculates a scattered radiation content rate S (x,y) from the calculated primary radiation image and scattered radiation image based on a formula (14). Note that the scattered radiation content rate S (x,y) takes a value from 0 to 1.

$$Icp(x,y)=Io(x,y) \times \exp(-\mu \times T(x,y)) \quad (12)$$

$$Ics(x,y)=Io(x,y) * S\sigma(T(x,y)) \quad (13)$$

$$S(x,y)=Ics(x,y)/(Ics(x,y)+Icp(x,y)) \quad (14)$$

where: (x,y) is the coordinate of the processing target pixel of the radiation image in the small image area; Icp (x,y) the primary radiation image at the processing target pixel (x,y); Ics (x,y) is the scattered radiation image at the processing target pixel (x,y); Io (x,y) is the incident dose on the subject surface at the processing target pixel (x,y); $\mu$ is the linear attenuation coefficient; and S$\sigma$(T (x,y)) is the convolution kernel representing scattering characteristics according to the subject thickness at the processing target pixel (x,y). The formula (12) is based on a known exponential decay law and the formula (13) is based on the method described in J. M. Boone et al., "An analytical model of the scattered radiation distribution in diagnostic radiology", Am. Assoc. Phys. Med. Vol. 15, No. 5, pp. 721-725, 1988 (Reference Literature 1)". The incident dose 10 (x,y) on the subject surface may take any value, such as a value of 1, because, even if any value is defined, it is cancelled by the division in the calculation of S (x,y).

Here, "*" in formula (13) is an operator representing a convolution operation. The nature of the kernel varies with radiation field distribution, subject composition distribution, and radiography conditions (i.e., tube voltage, mAs value, radiography distance, air gap amount, characteristics of the radiation detector at the time of radiography, and the like) other than the thickness of the subject. According to the method described in Reference Literature 1, the scattered radiation may be approximated by the convolution of the point spread function S$\sigma$(T (x,y)) in the formula (13)) with respect to the primary radiation. The S$\sigma$(T (x,y)) may be obtained experimentally according to the radiation field information, the subject information, the radiography conditions, and the like. The convolution is performed using pixels in the small image area S0.

The S$\sigma$(T (x,y)) may be calculated based on the radiation field information, the subject information, and the radiography conditions at the time of radiography, but in the present embodiment, a table associating various types of radiation field information, various types of subject information, and various types of radiography conditions with S$\sigma$(T (x,y)) is stored in the storage unit 28, and the S$\sigma$(T (x,y)) is obtained with reference to the table based on the radiation field information, the subject information, and the radiography conditions at the time of radiography. Further, the S$\sigma$ (T (x,y)) may be approximated by the T (x,y).

The scattered radiation elimination unit 27 performs scattered radiation elimination processing by reducing the frequency component in a frequency band that can be deemed as scattered radiation in the radiation image based on virtual grid characteristics and scattered component information. For this purpose, the scattered radiation elimination unit 27 performs frequency decomposition on the radiation image of the small image area S0 to obtain a frequency component of each of a plurality of frequency bands, performs processing to reduce the gain of at least one frequency component, and combines the processed frequency component and the rest of the frequency components, thereby obtaining a radiation image processed by the scattered radiation elimination processing. As for the frequency decomposition method, any known method, such as wavelet transformation, Fourier transformation, and the like, may be used in addition to a method that performs a multi-resolution conversion on the radiation image.

The scattered radiation elimination unit 27 calculates a conversion factor R (x,y) from a scattered radiation transmission factor Ts and a primary radiation transmission factor Tp which are the virtual grid characteristics, and the scattered radiation content rate S (x,y) by a formula (15) given below.

$$R(x,y)=S(x,y) \times Ts+(1-S(x,y)) \times Tp \quad (15)$$

As the scattered radiation transmission factor Ts and primary radiation transmission factor Tp, and the scattered radiation content rate S (x,y) take a value from 0 to 1, the conversion factor R (x,y) also takes a value from 0 to 1. The scattered radiation elimination unit 27 calculates the conversion factor R (x,y) for each of a plurality of frequency bands in the small image area S0.

In the description that follows, a pixel value of a processing target pixel in a small image area S0 is expressed as I (x,y), a frequency component image that can be obtained by frequency decomposition at the processing target pixel is expressed as I (x,y,r), a frequency composite is expressed as I (x,y)=$\Sigma r$I (x,y,r), a conversion factor with respect to each frequency band is expressed as R (x,y,r), and a scattered radiation transmission factor and a primary radiation transmission factor with respect to each frequency band are expressed as Ts (r) and Tp (r) respectively. Note that "r" represents a hierarchy of frequency bands, indicating that the greater the "r" the lower the frequency. Thus, I (x,y,r) is a frequency component image of a certain frequency band. As for the scattered radiation content rate S (x,y), the scattered radiation content rate of the radiation image may be used directly, but a scattered radiation content rate may be obtained with respect to each frequency band, as in the scattered radiation transmission factor Ts and the primary radiation transmission factor Tp.

In the present embodiment, the conversion factor R (x,y,r) is calculated with respect to each frequency component, then a frequency component image I (x,y,r) is converted by multiplying the frequency component image I (x,y,r) with a conversion factor R (x,y,r) of the corresponding frequency band, and a frequency component image I (x,y,r) multiplied by the conversion factor R (x,y,r) (i.e., I (x,y,r)×R (x,y,r)) is frequency combined, thereby obtaining a processed radiation image I' (x,y). Therefore, the processing performed in the scattered radiation elimination unit 27 may be expressed by a formula (16) given below. As the conversion factor R (x,y,r) takes a value from 0 to 1, the multiplication of a frequency component with a conversion factor R (x,y,r) of the corresponding frequency band reduces the pixel value, i.e., the gain at the processing target pixel (x,y) of the frequency component.

$$I'(x, y) = \sum_r \{I(x, y, r) \times R(x, y, r)\} \quad (16)$$

$$= \sum_r \{I(x, y, r) \times (S(x, y) \times Ts(r) + (1 - S(x, y)) \times Tp(r))\}$$

Here, in the present embodiment, a small image area S0 is frequency decomposed into six frequency bands, and a scattered radiation transmission factor Ts and a primary radiation transmission factor Tp are obtained for the six frequency bands. In this case, the scattered radiation transmission factors Ts and the primary radiation transmission factors Tp take, for example, the values shown in a formula (17) given below. Note that a value on the more right side in the formula (17) represents a value of a lower frequency band.

$$Ts=\{0.7, 0.7, 0.7, 0.7, 0.3, 0.2\}$$

$$Tp=\{0.7, 0.7, 0.7, 0.7, 0.7, 0.7\} \quad (17)$$

As shown in the formula (17), scattered radiation transmission factors Ts and primary radiation transmission factors Tp have the same value in high frequency bands (r=1 to 4), but scattered radiation transmission factors Ts take smaller values in low frequency bands (r=5 to 6). This is because the grid has a higher elimination rate for a lower frequency band in which a frequency component of scattered radiation is predominant, but the frequency dependence of the elimination rate is low with respect to primary radiation.

Figure 14:
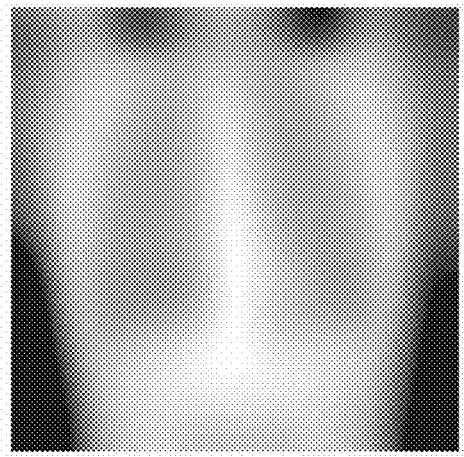
FIG. 14 illustrates a scattered radiation content rate distribution in a chest radiation image.
Figure 15:
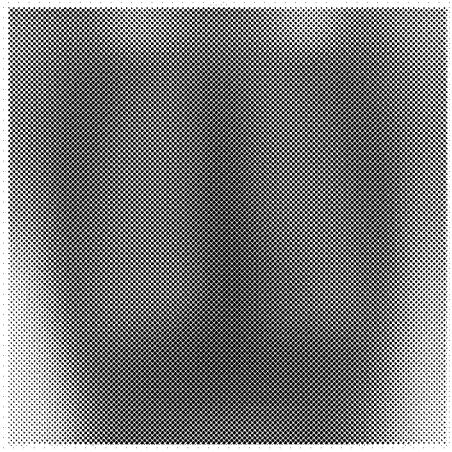
FIG. 15 illustrates a conversion factor calculated in case of illustrating the scattered radiation content distribution shown in FIG. 14.

FIG. 14 illustrates a distribution of scattered radiation content rate S (x,y) in a chest radiation image. FIG. 14 shows a radiation image corresponding to a chest region in a small radiation image, not in a small image area. In FIG. 14, the higher the scattered radiation content rate S (x,y), the higher the brightness at each pixel position. FIG. 14 shows that the mediastinal region and the surrounding of the lung fields have a high scattered radiation content rate in the chest image. Conversion factors calculated based on the formulae (15) and (17) are shown in FIG. 15 in case that such a distribution of scattered radiation content rate S (x,y) is indicated. In FIG. 15, lower brightness has a lower value and the pixel value is more reduced. A comparison between FIG. 14 and FIG. 15 shows that the mediastinal region and the surrounding of the lung fields having a high scattered radiation content rate have a small conversion factor. Therefore, in a processed radiation image obtained by performing the processing shown in the formula (16) using the conversion factors calculated in the foregoing manner, scattered components are eliminated according the type of grid assumed to be used.

Note that the scattered radiation elimination unit 27 may eliminate scattered radiation of a radiation image in the following manner. In case that a frequency composite is expressed as I (x,y)=ΣrI (x,y,r) as in the above, the scattered radiation elimination unit 27 first decomposes a frequency component image I (x,y,r) into a scattered component Ics (x,y,r) and a primary radiation component Icp (x,y,r) by a formula (18) given below using the scattered radiation content rate S (x,y).

$$Ics(x,y,r)=S(x,y) \times I(x,y,r)$$

$$Icp(x,y,r)=(1-S(x,y)) \times I(x,y,r) \quad (18)$$

Further, the scattered radiation elimination unit 27 performs an image conversion on each of the scattered component Ics (x,y,r) and the primary radiation component Icp (x,y,r) by a formula (19) given below by applying the scattered radiation transmission factor Ts (r) and the primary radiation transmission factor Tp (r) which are the virtual grid characteristics, thereby calculating converted scattered component Ics' (x,y,r) and primary radiation component Icp' (x,y,r).

$$Ics'(x,y,r)=Ics(x,y,r) \times Ts(r)=S(x,y) \mid (x,y,r) \times Ts(r)$$

$$Icp'(x,y,r)=Icp(x,y,r) \times Tp(r)=(1-S(x,y)) \times I(x,y,r) \times Tp(r) \quad (19)$$

Then, the scattered radiation elimination unit 27 frequency combines the scattered component Ics' (x,y,r) and the primary radiation component Icp' (x,y,r) by a formula (20) given below, thereby calculating a processed radiation image I (x,y)' for the processing target pixel position.

$$I'(x, y) = \sum_r \{Ics'(x, y, r) + Icp'(x, y, r)\} \quad (20)$$

$$= \sum_r \{S(x, y) \times I(x, y, r) \times Ts(r) + (1 - S(x, y)) \times I(x, y, r) \times Tp(r)\}$$

$$= \sum_r \{I(x, y, r) \times (S(x, y) \times Ts(r) + (1 - S(x, y)) \times Tp(r))\}$$

The scattered radiation elimination unit 27 calculates a processed radiation image I (x,y)' with respect to all processing target pixel positions and terminates the scattered radiation elimination processing. Note that the processed radiation image is displayed on the display unit 6 or, otherwise, stored in a database (not shown).

In this way, in the first embodiment, in performing image processing based on scattered radiation on a processing target area, another area adjacent to the processing target area in a radiation image G0 is added to the processing target area, and the image processing based on scattered radiation is performed on the processing target area using the another area and the processing target area. Therefore, the image processing based on scattered radiation may be performed on a processing target area by also taking into account the influence of another area adjacent to the processing target area, whereby the image processing based on scattered radiation may be performed accurately on the processing target area.

Further, in a case in which a radiation image G0 is formed of a plurality of small radiation images G1 to G4 joined together, as in the radiation image obtained by radiography using the long radiation detector shown in FIG. 2, and one of the small radiation images is set as the processing target image, the performance of image processing by adding at least one another small radiation image adjacent to the small radiation image set as the processing target image as the another area allows the image processing based on scattered radiation to be performed accurately on the radiation image obtained by radiography using the long radiation detector.

Further, a scattered radiation component at a processing target pixel in a processing target area is influenced largely by a scattered radiation component in an area adjacent to the processing target pixel, but not influenced so much by a scattered radiation component in an area away from the processing target pixel. Therefore, in performing image processing on a processing target pixel in a processing target area, the amount of computations for the image processing may be reduced by setting a small image area S0 smaller than the processing target area for the processing target pixel and performing image processing based on the information of the small image area S0, whereby the image processing based on scattered radiation may be performed rapidly.

In this case, by setting a small image area S0 according to the position of the processing target pixel, a small image area S0 appropriate for the position of the processing target pixel may be set, so that the image processing based on scattered radiation may be performed accurately, while reducing the amount of computations.

By setting a small image area S0 having the size according to the body thickness of a subject in a processing target area, for example, a small image area S0 having a larger size may be set for a processing target area corresponding to a thick body portion, so that the image processing based on scattered radiation may be performed accurately, while reducing the amount of computations.

Further, the use of parameters used in image processing for a certain small image area S0 in the image processing for another small image area allows the amount of computations for calculating the parameter to be reduced, so that the body thickness estimation processing and scattered radiation elimination processing may be performed more rapidly.

In the first embodiment described above, in case that the scattered radiation elimination processing for one small radiation image in a processing target image is completed, only the processed small radiation image may be displayed on the display unit 6 before performing the processing for another small radiation image.

Further, image processing may be performed in priority order from a processing target area which includes a small radiation image corresponding to a thick body portion of the subject M. The "thick body portion" refers to, for example, a portion of a small radiation image having a large average thickness. This results in that the image processing based on scattered radiation is performed in order from an area most effective of the image processing based on scattered radiation. Therefore, by sequentially displaying the processed small radiation images, the area most effective of the image processing based on scattered radiation may be confirmed earlier, and as a result, image processing results may be confirmed efficiently. Here, the body thickness of the subject M may be estimated by the foregoing method or may be obtained by a sensor or the like, a thick body thickness portion of the subject M.

In the first embodiment described above, the scattered radiation elimination processing is performed after the body thickness estimation processing is completed for all processing target pixels, but the body thickness estimation processing and the scattered radiation elimination processing may be performed sequentially for all processing target pixels. That is, body thickness estimation processing and scattered radiation elimination processing may be performed on one processing target image and then the processing target pixel is set to the next pixel.

Further, in the first embodiment described above, a small image area S0 is set and image processing based on scattered radiation is performed on a processing target pixel using information of the small image area S0, but the image processing based on scattered radiation may be performed without setting the small image area S0. In this case, the image processing based on scattered radiation may be performed on each processing target area that includes another adjacent area, as described above.

In the first embodiment described above, there may be a case in which the characteristics of the detectors that detect small radiation images G1 to G4 respectively differ slightly from each other, thereby causing a difference in density between each of the obtained small radiation images G1 to G4. Therefore, the image processing is preferably performed after correction processing for aligning the characteristics of each detector is performed.

Figure 16:
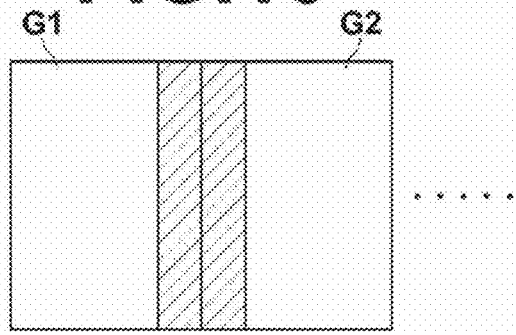
FIG. 16 illustrates a predetermined range at the boundary of a small radiation image.

Further, as each detector corresponds to a different region of a subject, in case that body thickness estimation is performed, there may be a case in which a different body thickness is calculated in each detector. In this case, a density step may possibly occur in the processed radiation image at the boundary between each of the small radiation images G1 to G4. Here, in case that the body thicknesses at the boundary of adjacent small radiation images correspond to each other, the density step does not occur after the scattered radiation elimination processing is performed. Therefore, estimated body thicknesses are preferably matched at the boundary of small radiation images. In this case, as for the value of the body thickness at the boundary, an average value or either one of the adjacent body thicknesses at the boundary may be used. Here, in case that the value of body thickness at the boundary is set to the average value of the adjacent body thicknesses, it is preferably that the value of the body thickness is changed in a given range, including the boundary, as illustrated in FIG. 16 (indicated by diagonal lines), so as to gradually correspond to the value of each small radiation image with distance from the boundary. This causes the body thickness at the boundary between the radiation image G1 and the radiation image G2 to be changed gradually, so that the density step at the boundary of small radiation images may be prevented in a processed image obtained by scattered radiation elimination processing. Note that, in the present embodiment, body thicknesses estimated at the boundary of adjacent small radiation images may be within a predetermined tolerance, as well as matching completely with each other.

Figure 17:
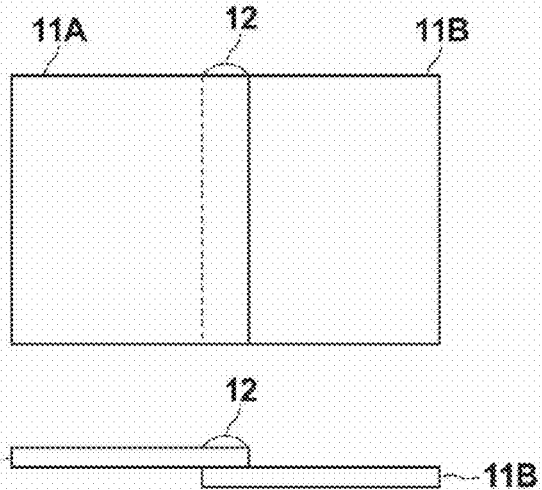
FIG. 17 illustrates an overlap of detectors.

Still further, in the first embodiment described above, in the case in which the detectors 11A to 11D are disposed so as to partially overlap with each other, the influence of scattered radiation is increased in the detector located on the backward side of the X-ray source 3 at the joining portion where the detectors overlap with each other. For example, in the joining portion 12 between the detector 11A and the detector 11B shown in FIG. 17, the influence of scattered radiation is increased in the detector 11B located on the backward side of the X-ray source 3. Note that FIG. 17 shows only the detector 11A and the detector 11B for the sake of explanation. In case that the influence of scattered radiation is increased in the detector located on the backward side as described above, the body thickness determined by the body thickness determination unit 26 at the joining portion of detectors may possibly be an abnormal value, differing largely from the body thickness determined at a portion other than the joining portion. In this case, a density step occurs at the boundary between small radiation images in a processed radiation image obtained by the scattered radiation elimination processing. Therefore, it is preferable that a determination is made as to whether or not the body thickness at the joining portion is an abnormal value, and in case that it is determined to be an abnormal value, the scattered radiation elimination processing is performed by determining the body thickness without using the body thickness of the abnormal value. Hereinafter, body thickness determination processing in this case will be described.

Here, as the positions of the joining portions of the detectors 11A to 11D in the radiation detector 5 are known, the positions are stored in the storage unit 28. Then, the body thickness determination unit 26 determines body thicknesses first, as in the first embodiment. Then, the body thickness determination unit 26 obtains information of the positions of the joining portions and determines whether or not the determined body thicknesses at the joining portions are abnormal values. The determination as to whether or not a body thickness is an abnormal value may be made by calculating an absolute value of difference between the body thickness at the position of a joining portion and the body thickness at a position other than the positions of the joining portions, and determining whether or not the absolute value of difference exceeds a predetermined threshold value.

Figure 18:
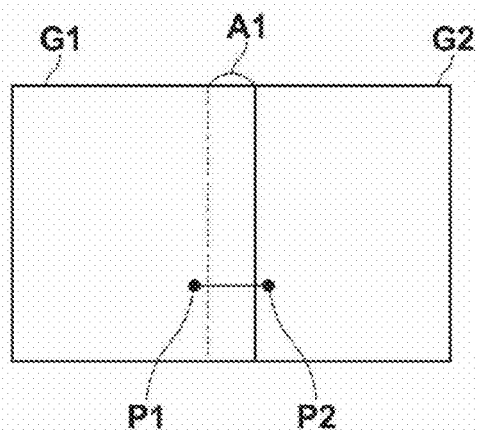
FIG. 18 illustrates a joining portion of radiation images.

Then, in case that the body thickness is determined to be an abnormal value, the body thickness determination unit 26 detects a pixel P1 of the small radiation image G1 and a pixel P2 of the small radiation image G2 adjacent to a joining portion A1, as illustrated in FIG. 18. In this case, the small radiation image G1 and the small radiation image G2 adjacent to the joining portion A1 are adjacent areas. Then, an interpolation operation is performed in the arrangement direction of the small radiation image G1 and the small radiation image G2 using a body thickness determined at the pixel P1 and a body thickness determined at the pixel P2, thereby calculating a body thickness at each pixel in the joining portion A1 and determining the calculated body thickness as the body thickness at the joining portion A1. The use of the body thickness determined in the foregoing manner allows the scattered radiation elimination processing to be performed without being influenced by an abnormal value of the body thickness that occurs at the joining portion of each of the detectors 11A to 11D.

Figure 19:
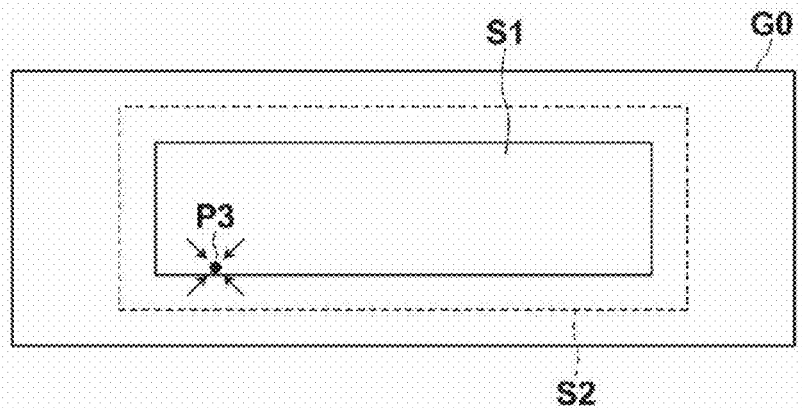
FIG. 19 illustrates setting of a processing target area in a second embodiment.

Next, a second embodiment of the present invention will be described. In the first embodiment described above, a processing target area is set in a radiation image G0 that combines small radiation images G1 to G4, and further a small image area S0 is set, but the second embodiment differs from the first embodiment in that, in the second embodiment, a processing target area is set by trimming the radiation image G0. FIG. 19 illustrates the setting of a processing target area in the second embodiment. As illustrated in FIG. 19, it is assumed that the processing target area S1 is set by trimming the radiation image G0. In such a case, in case that image processing based on scattered radiation is performed using only the processing target area S1, not all of the scattered radiation that influences a pixel P3 located at an end portion of the processing target area S1 cannot be taken into account. For this reason, in the second embodiment, an area S2 surrounding the processing target area S1 is added to the processing target area S1, and scattered radiation elimination processing is performed on the processing target area S1 (excepting the area S2) using information of the processing target area S1 added with the area S2.

This allows a scattered radiation component of another area adjacent to the processing target area to be used, as in the first embodiment, so that the image processing based on scattered radiation may be performed accurately on the processing target area.

Figure 20:
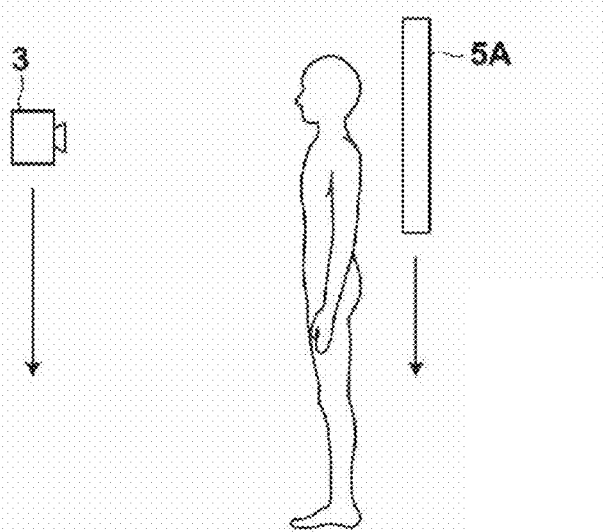
FIG. 20 illustrates long length radiography.

In the first and the second embodiments described above, a radiation image obtained using a long radiation detector is used as the processing target, but the present invention is also applicable to the case in which scattered radiation elimination processing is performed on a radiation image obtained by so-called long length radiography in which a radiation source 3 and a normal sized radiation detector 5A are moved synchronously along a subject and radiography is performed at each moved position, as illustrated in FIG. 20. That is, the radiation image obtained by the long length radiography and the radiation image obtained using the long radiation detector are substantially the same, other than that the radiography methods are different. Therefore, it is possible to set a processing target area and further a small image area, and to perform scattered radiation elimination processing, as in the first embodiment, on an image obtained by long length radiography by assuming a radiation image obtained at each radiography position as each of the radiation images G1 to G3 in the first embodiment.

Further, in the first and the second embodiments described above, an arrangement may be adopted in which the radiation image G0 is reduced, then body thickness estimation processing is performed using the reduced radiation image, and a processing target area is set and scattered radiation elimination processing is performed on the radiation image G0 using the estimation result. For example, a body thickness distribution Tn estimated by the body thickness estimation processing using the reduced radiation image may be used as the initial body thickness distribution T0 (x,y). This allows the scattered radiation elimination processing to be performed efficiently.

Still further, in the first and the second embodiments described above, an arrangement may be adopted in which the processed radiation image is displayed to allow the operator to correct the degree of elimination of scattered radiation. In this case, it is preferable that a change in the degree of elimination of scattered radiation for a certain processing target area causes the degree of elimination of scattered radiation for the other processing target areas to be changed in conjunction therewith.

Further, in the first and the second embodiments described above, the scattered radiation elimination processing is performed using a radiation image obtained by a system that captures a radiation image of a subject using the radiation detector 5, but it should be appreciated that the present invention is also applicable to the case in which a radiation image obtained by cumulatively storing radiation image information of a subject on a storage phosphor sheet, as the radiation detecting body, as described, for example in Japanese Unexamined Patent Publication No. 8 (1996)-266529 and Japanese Unexamined Patent Publication No. 9 (1997)-022039, and photoelectrically reading out from the storage phosphor sheet is used.

Hereinafter, advantageous effects of the embodiments of the present invention will be described.

In a case in which a radiation image is formed of a plurality of small radiation images smaller in area than the radiation image combined together, as a radiation image obtained by radiography using, for example, a long radiation detector, and one of the small radiation images is set as a processing target image, the performance of image processing by adding at least one another small radiation image adjacent to the small radiation image to the processing target image, as another area, allows the image processing based on scattered radiation to be performed accurately on the radiation image obtained by radiography using the long radiation detector.

The performance of image processing in priority order from a processing target area which includes a small radiation image corresponding to a thick body portion of the subject results in that the image processing based on scattered radiation is performed in order from an area most effective of the image processing based on scattered radiation. Therefore, by sequentially displaying the processed small radiation images, the area most effective of the image processing based on scattered radiation may be confirmed earlier, so that image processing results may be confirmed efficiently.

Further, a scattered radiation component of a processing target pixel in a processing target area is influenced greatly by a scattered radiation component in an area adjacent to the processing target pixel, but not influenced so much by a scattered radiation component in an area away from the processing target pixel. Therefore, in performing image processing on a processing target pixel in a processing target area, the setting of a small image area smaller than the processing target area for the processing target pixel and performance of image processing based on scattered radiation on the basis of information of the small image area allow the image processing based on scattered radiation to be performed by taking into account the influence of a scattered radiation component included in another area while reducing the amount of computations for the image processing, whereby the image processing based on scattered radiation may be performed rapidly and accurately.

In this case, by setting a small image area according to the position of the processing target pixel, a small image area appropriate for the position of the processing target pixel may be set, so that the image processing based on scattered radiation may be performed accurately, while reducing the amount of computations.

Further, by setting a small image area having a size according to the body thickness of a subject in a processing target area, for example, a small image area having a larger size may be set for a processing target area corresponding to a thicker body portion, so that the image processing based on scattered radiation may be performed accurately, while reducing the amount of computations.

Further, the use of a parameter used in image processing for one small image area in image processing for another small image area allows the amount of computations for calculating the parameter to be reduced, so that the image processing based on scattered radiation may be performed more rapidly.

What is claimed is:

1. A radiation image processing apparatus that performs image processing on a radiation image based on scattered radiation generated by the subject, the radiation image being obtained without using an anti-scatter grid when capturing, the apparatus comprising:
   a receiver which receives the radiation image captured by applying radiation to a subject;
   a processor, which comprises:
   an area setting unit which sets a target area, and which adds another area different from the target area in the radiation image to the target area for performing the image processing of the target area in the radiation image; and
   an image processing unit that performs the image processing of the target area using the another area and the target area,
   wherein the image processing comprises obtaining a scattered radiation component using said another area and the target area, and reducing the scattered radiation in the target area based on the scattered radiation component,
   wherein the area setting unit further sets, in performing the image processing on the target area being processed, a small image area smaller than the processing target area for a processing target pixel in the processing target area, and
   wherein the image processing unit performs the image processing based on information of the small image area.

2. The radiation image processing apparatus as claimed in claim 1, wherein, in case that the radiation image is formed of a plurality of small radiation images smaller in area than the radiation image and one of the small radiation images is set as a processing target image, the area setting unit adds at least one other small radiation image different from the small radiation image set as the processing target image to the processing target area as the another area.

3. The radiation image processing apparatus as claimed in claim 1, wherein the area setting unit sets the small image area according to the position of the processing target pixel.

4. The radiation image processing apparatus as claimed in claim 1, wherein the area setting unit sets the small image area having a size according to a body thickness or a radiography region of a subject in the target area being processed.

5. The radiation image processing apparatus as claimed in claim 1, wherein the image processing unit performs the image processing on another image area using a parameter of the image processing performed on one small image area.

6. The radiation image processing apparatus as claimed in claim 2, wherein the at least one other small radiation image is a small radiation image adjacent to the small radiation image set as the processing target image.

7. The radiation image processing apparatus as claimed in claim 2, wherein the image processing unit performs the image processing in priority order from a small radiation image corresponding to a thick body portion of the subject.

8. The radiation image processing apparatus as claimed in claim 2, wherein the radiation image is formed of the plurality of small radiation images combined together.

9. The radiation image processing apparatus as claimed in claim 8, wherein, in case that the radiation image is formed of the small radiation images combined so as to partially overlap with each other and an abnormality occurs in a result of the image processing in an area where the small radiation images are overlapped, the image processing unit performs the image processing using an adjacent area adjacent to the area where the small radiation images are overlapped.

10. A radiation image processing method that performs image processing on a radiation image based on scattered radiation generated by the subject, the radiation image being obtained without using an anti-scatter grid when capturing, the method comprising:
    receiving the radiation image captured by applying radiation to a subject;
    setting, by a processor, a target area;
    adding another area different from the target area in the radiation image to the target area for performing the image processing of the target area in the radiation image; and
    performing the image processing of the target area using the another area and the target area,
    wherein the image processing comprises obtaining a scattered radiation component using said another area and the target area, and reducing the scattered radiation in the target area based on the scattered radiation component,
    wherein, in said performing the image processing on the processing target area, setting a small image area smaller than the processing target area for a processing target pixel in the processing target area, and
    wherein the image processing is performed based on information of the small image area.

11. A non-transitory computer-readable recording medium containing a radiation image processing program for causing a computer to perform a radiation image processing method that performs image processing on a radiation image based on scattered radiation generated by the subject, the radiation image being obtained without using an anti-scatter grid when capturing, the program causing the computer to perform the steps of:
  receiving the radiation image captured by applying radiation to a subject;
  setting a target area;
  adding another area different from the target area in the radiation image to the target area for performing the image processing of the target area in the radiation image; and
  performing the image processing of the target area using the another area and the target area,
  wherein the image processing comprises obtaining a scattered radiation component using said another area and the target area, and reducing the scattered radiation in the target area based on the scattered radiation component,
  wherein, in performing the image processing on the processing target area, setting a small image area smaller than the processing target area for a processing target pixel in the processing target area, and
  the image processing is performed based on information of the small image area.

* * * * *